United States Patent
Iaquinta et al.

(10) Patent No.: US 7,116,750 B1
(45) Date of Patent: Oct. 3, 2006

(54) METHOD FOR DETECTING AND MEASURING A SECONDARY MATERIAL INTERMITTENTLY DEPOSITED TO A MOVING SUBSTRATE

(75) Inventors: Michael Iaquinta, Westerville, OH (US); David Pond, Dublin, OH (US); John W. Pettit, Derwood, MD (US)

(73) Assignee: Automation and Control Technology, Inc., Columbus, OH (US)

( * ) Notice: Subject to any disclaimer, the term of this patent is extended or adjusted under 35 U.S.C. 154(b) by 134 days.

(21) Appl. No.: 11/004,277

(22) Filed: Dec. 2, 2004

(51) Int. Cl.
*G01N 23/06* (2006.01)

(52) U.S. Cl. .......................................... 378/53; 378/51
(58) Field of Classification Search ................ 378/50, 378/51, 53–56; 250/548
See application file for complete search history.

(56) References Cited

U.S. PATENT DOCUMENTS

| | | | | |
|---|---|---|---|---|
| 3,697,754 A | * | 10/1972 | Maxwell | 378/54 |
| 7,020,239 B1 | * | 3/2006 | Sikora | 378/50 |
| 2001/0014138 A1 | * | 8/2001 | Knigge et al. | 378/57 |

* cited by examiner

*Primary Examiner*—Edward J. Glick
*Assistant Examiner*—Jurie Yun
(74) *Attorney, Agent, or Firm*—Standley Law Group LLP

(57) ABSTRACT

A method for detecting and measuring regions of a secondary material deposited onto a moving substrate. The method employs an x-ray source for directing an x-ray beam at the moving substrate, and an x-ray detector to detect an amount of x-ray energy transmitted by the moving sheet of material. Areas of bare substrate will allow for different amounts of x-ray transmission than areas of the substrate containing the secondary material. These differences in transmission and/or absorption can be used to detect the location of a region of secondary material and to determine if it falls within an acceptable range. According to one particular embodiment of the present invention, the method can be used to analyze burn characteristic modifying bands of a secondary material intermittently and repeatedly deposited to a moving web of smoking article paper.

40 Claims, 4 Drawing Sheets

METHOD FOR DETECTING AND MEASURING A SECONDARY MATERIAL INTERMITTENTLY DEPOSITED TO A MOVING SUBSTRATE

BACKGROUND AND SUMMARY OF THE INVENTION

The present invention is directed to an apparatus and method for detecting and measuring a secondary material that has been deposited at intermittent intervals onto a moving substrate. More particularly, the apparatus and method of the present invention employs at least one x-ray emitter located on a first side of the moving substrate, and at least one x-ray detector located on the opposite side of the moving substrate.

Various devices exist for measuring the thickness of materials, including moving materials. Contact gauges and similar other measurement devices that require physical communication with the material to be measured have been known for many years. More recently, non-contact measurement devices have been developed that allow for the measurement of various characteristics of a moving material sample, without the need for physical communication between the material and the device. These devices may include, for example, a source of radiation and a means to detect the source of radiation after it interacts with the moving material sample.

A number of these non-contact measurement devices were developed for use in the manufacturing of sheet (roll) steel. These devices have been used to measure thickness, or slight variations in thickness that may occur over the unrolled length of a steel coil. Such devices have also been used in the paper manufacturing industry to measure, for example, the typical basis weight or moisture content of a moving paper web. These devices have further been used to measure the thickness of a coating or film that has been deposited onto the surface of a moving sheet of material. For example, the devices may be used to measure the average coating thickness across a painted or treated sheet of metal, or to measure the thickness of a protective (aseptic) coating layer deposited on to the moving stock for a food or beverage carton. Thus, typically, such devices have been used to measure a dimension or characteristic that is substantially constant, or that varies only slightly and over a considerable period of time. Many of these known devices operate by measuring reflected (back-scattered) radiation.

It is also desirable, however, to be able to detect and measure a secondary (additive) material that is deposited onto a moving substrate intermittently, rather than substantially uniformly across its surface. For example, in certain manufacturing processes, it may be necessary or desirable to deposit or apply an additive to a moving substrate in a manner that produces only intermittent, repetitive regions of the additive. Most commonly, such regions would extend across the width of the moving substrate. The regions may be deposited at regular or irregular intervals onto the substrate.

One particular such process of interest involves the treatment of a moving web of a paper substrate that will eventually be used to produce cigarettes or other similar smoking articles. As the moving paper web is expelled from a paper-making machine or other manufacturing or treatment device, one or more additives may be periodically deposited thereon. More particularly, for example, intermittent regions (bands) of a self-extinguishing additive or some other material may be deposited in rows that extend substantially across the width of the paper substrate. Such periodic additive deposits may be used, for example, to produce a modification of the burn characteristics of a cigarette or other smoking article that is later produced from the paper substrate. More specifically, the additive(s) may be selected and deposited in such a manner that a smoking article produced from the paper web will have reduced static burn characteristics, or may be entirely self-extinguishing when left in a static condition for a certain period of time.

In order to achieve such a desired end result, it is generally necessary to carefully control how the secondary material is deposited onto the substrate. For example, aside from ensuring that the secondary material is deposited onto the substrate at the location or interval desired, it is also typically required to precisely control the amount of secondary material that is deposited. For purposes of further illustration, and not limitation, it is known that in the exemplary process described above, wherein a self-extinguishing additive is deposited at repeating intervals to a moving web of smoking article paper, the amount of deposited self-extinguishing additive must be carefully monitored and controlled. More specifically, it has been found that the self-extinguishing additive must be deposited onto the paper substrate within a narrow thickness range in order to produce the desired static self-extinguishing characteristic without also causing the smoking article to self-extinguish while being smoked.

Thus, as can be seen from the foregoing discussion, there exists a need for a method of detecting and measuring a secondary material that is deposited onto a moving substrate at regular or irregular intervals. Such a method must be capable of accurately determining whether the secondary material deposits are within an acceptable thickness range, even when the thickness of such deposits is minimal. Such an apparatus must further be capable of accurately detecting and measuring substantially narrow regions or bands of the secondary material. Additionally, because the velocity of the moving substrate may be substantial, and the width of the secondary material deposits may be minimal, such a method must be capable of rapid measurement.

The method of the present invention satisfies this need. The method of the present invention preferably employs one or more X-ray apparatuses, each of which includes a preferably non-nucleonic x-ray emitter(s) and one or more corresponding x-ray detectors. Preferably, the x-ray emitter is located on one side of a moving substrate having known X-ray absorption characteristics, and is oriented to direct an x-ray beam at the moving substrate. The x-ray detector is preferably located on the opposite side of the moving substrate, and is located to receive an amount of the x-ray beam that passes through (is transmitted by) the moving substrate. The amount of the x-ray energy that is transmitted (or absorbed) by areas of bare substrate can be measured. The present invention is also able to measure the amount of the x-ray energy that is transmitted or absorbed by areas of the substrate containing a secondary material deposit. The difference in measurements of absorbed x-ray energy can be used to determine whether an acceptable amount of secondary material is present. By referencing known x-ray absorption properties of the substrate and/or additive materials, the measurements can be used to determine and report thickness, density or other material characteristics, if desired. Measurements can be reported in a variety of formats, such as, for example, whether the secondary material deposit is acceptable or unacceptable, or as an output of density, total thickness, secondary material thickness, or as a percentage thickness increase. The method of the present invention may also account for the fact that the substrate itself may not be of equal thickness across the whole of its length.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF THE EXEMPLARY EMBODIMENT(S)

Figure 1:
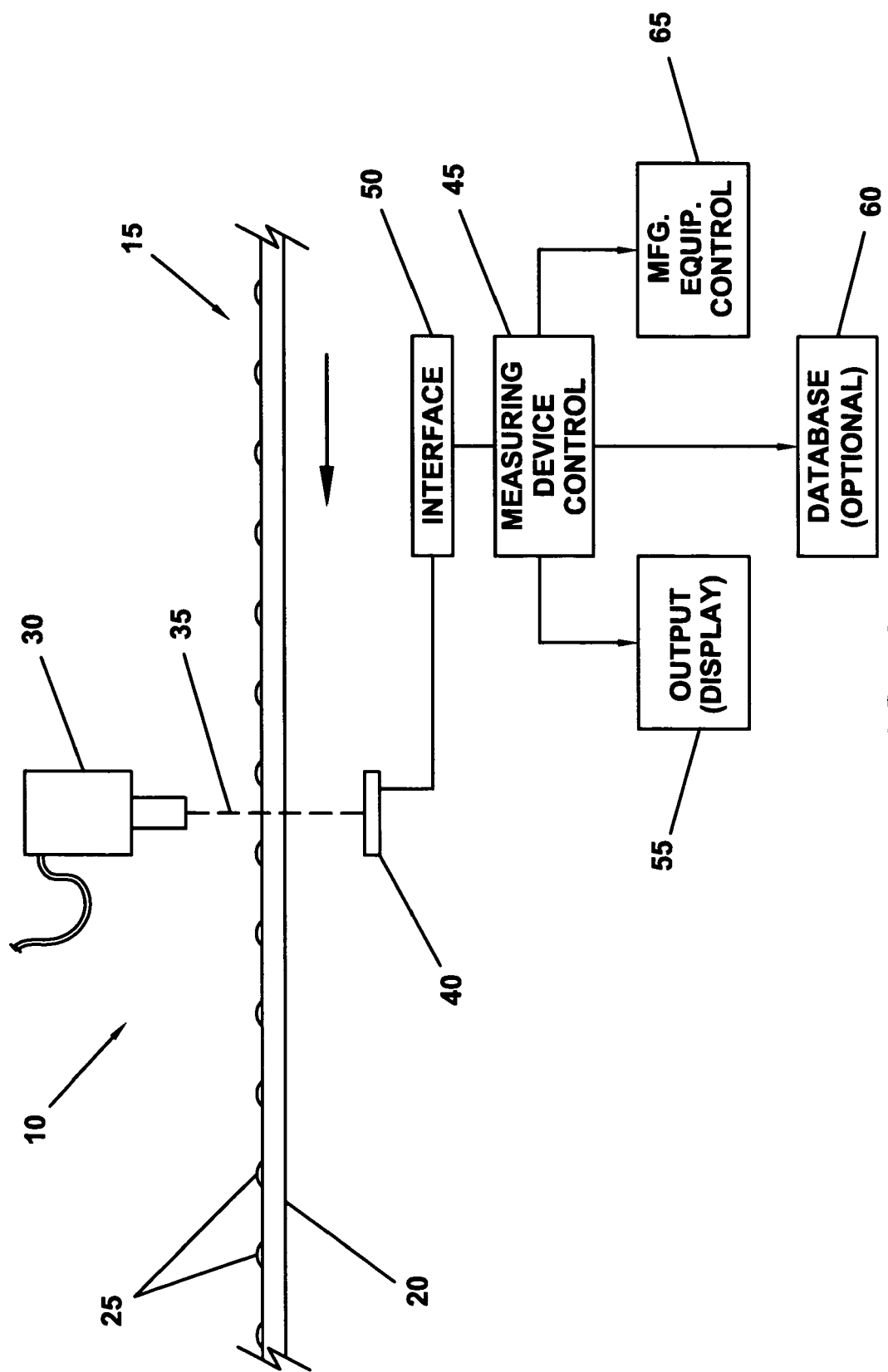
FIG. 1 depicts a side elevational view of a moving substrate having intermittent deposits of a secondary material as it is analyzed according to one embodiment of a thickness measurement method of the present invention.

An exemplary X-ray apparatus 10 that can be used in conjunction with the method of the present invention to detect and measure a secondary material that has been deposited to a substrate, can be observed in FIG. 1. In this particular example, the apparatus is deployed along a moving sheet of material 15. The moving sheet of material 15 consists of a substrate 20 having a secondary material 25 periodically deposited to the surface thereof.

As shown in FIG. 1, this particular embodiment of the X-ray apparatus 10 employs an x-ray emitter (emitter) 30 for directing an x-ray beam 35 onto the moving sheet of material 15. The X-ray apparatus 10 also employs a corresponding x-ray detector (detector) 40 for detecting an amount of x-ray energy that passes through (is transmitted by) the moving sheet of material 15. Thus, the emitter 30 is located on one side of the moving sheet of material 15, while the detector 40 is located on the opposite side thereof. One particular X-ray apparatus that can be acceptably used by the measurement method of the present invention is disclosed in a U.S. patent application entitled Detector Using Carbon Nanotube Material As Cold Cathode For Synthetic Radiation Source, which was filed on Dec. 16, 2003 by Dr. John W. Pettit and is hereby incorporated by reference herein.

Figure 3A:
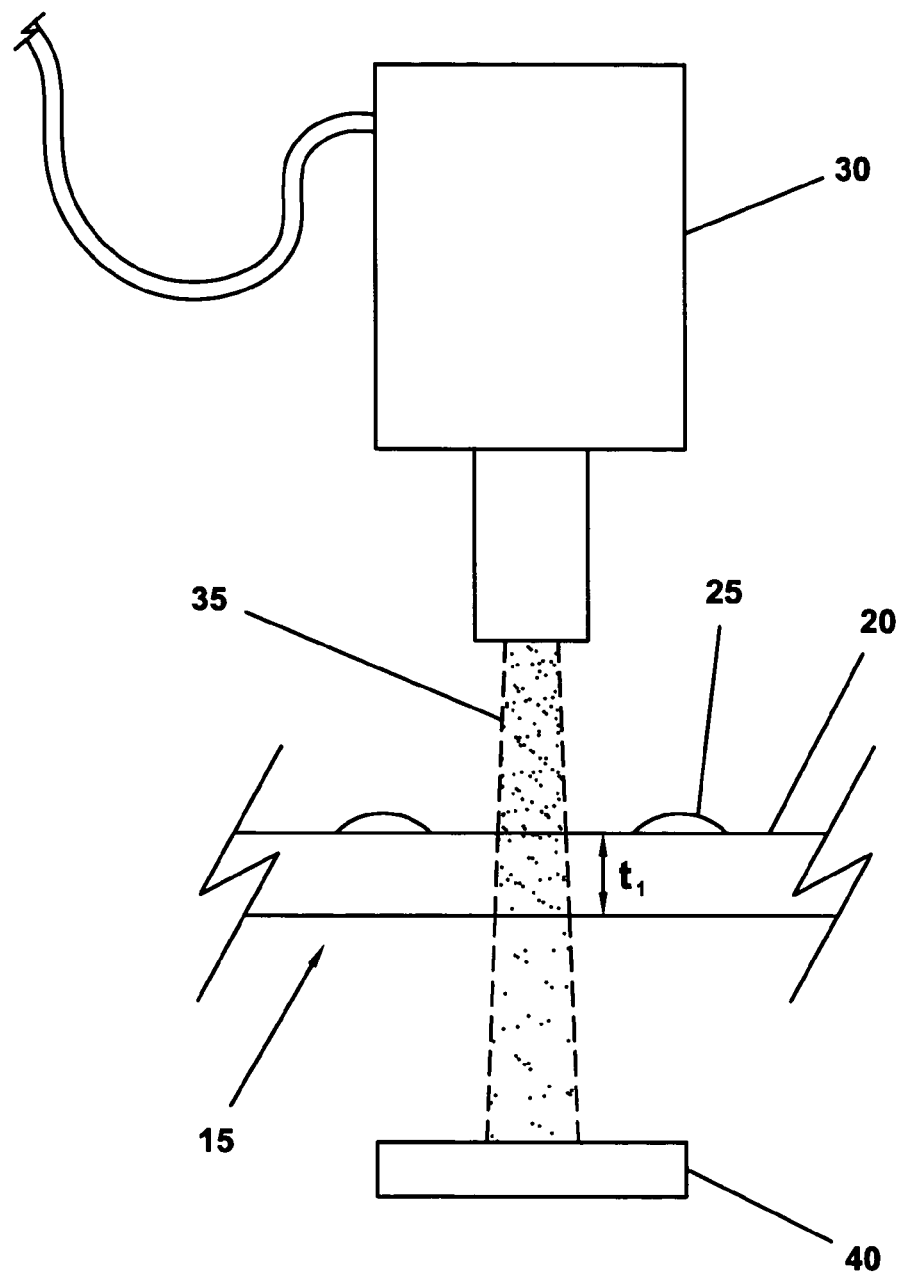
FIGS. 3a and 3b are enlarged views of the moving substrate an X-ray apparatus of FIG. 1, wherein the thickness of the moving substrate is measured according to the method of the present invention both in an area having no secondary material (i.e., in an area of bare substrate), and in an area having a deposit of secondary material, respectively.
Figure 3B:
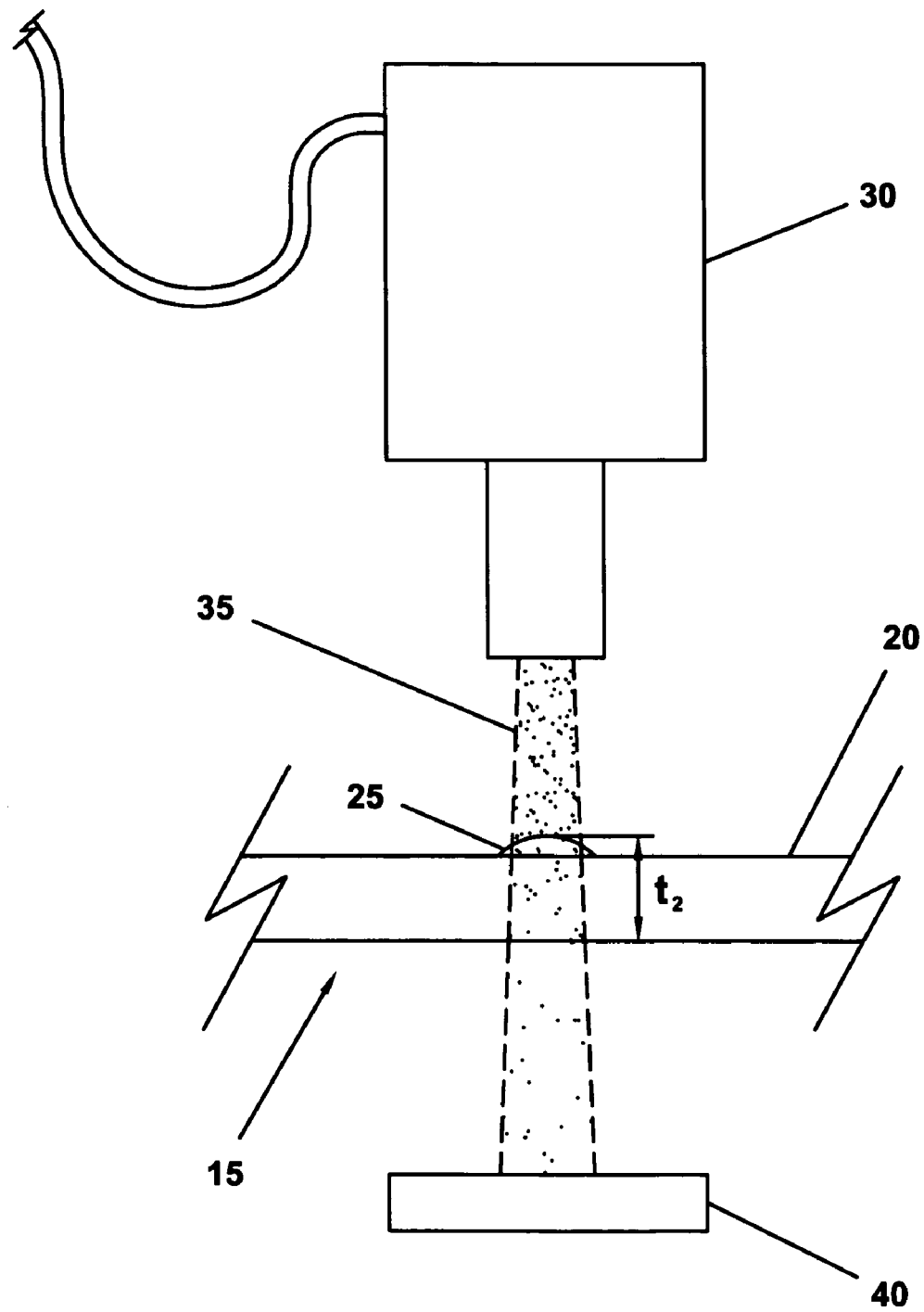

While in FIGS. 1 and 3a–3b the emitter 30 is shown to direct the x-ray beam 35 onto the moving sheet of material 15 at a substantially right angle, the x-ray beam may also impinge upon the moving sheet of material at other angles. Additionally, although in the particular embodiment of FIGS. 1 and 3a–3b the emitter 30 and detector 40 are shown to reside above and below the moving sheet of material 15, respectively, it should be understood that the orientation may also be reversed. In addition, more than one emitter 30 and more than one detector 40 may be utilized.

The X-ray apparatus 10 is preferably controlled by a control system 45 having a microprocessor. The X-ray apparatus 10 and the control system 45 may communicate electronically through an interface 50, which may utilize various electronics and/or software to properly present the data from the detector(s) 40 to the control system 45. The software may further include specialized algorithms that allow for a comparison of detector readings. Such algorithms may also various material characteristics such as thickness, density, or basis weight to be calculated using the amount of x-ray energy transmitted or absorbed by the moving sheet of material 15 (or the moving sheet of material and a region of secondary material 25) and the particular X-ray absorption characteristics of each material. The material characteristics may be output 55 in various forms. For example, material characteristics may be displayed on a monitor or similar display device, may be sent to a printer, or may be graphed or charted. Additionally, data relating to detector readings and/or various material characteristics may be saved in a database 60 for later use or analysis. It is also contemplated by the present invention that the processor may be in electronic communication with a control portion 65 of the equipment used to manufacture the substrate 20 and/or to deposit the secondary material 25 thereon. In such case, the control system 45 may analyze the material data and transmit instruction signals to the control portion 65 of the substrate manufacturing and/or secondary material deposition equipment based thereon. Additionally, or alternatively, the control system 45 may output and display messages to an operator of such equipment, instructing the operator to make necessary adjustments and/or stop the material 15 manufacturing process. In this manner, it can be ensured that the correct amount of secondary material is deposited on the substrate 20. Signals output from the detector 40 may be in either analog or digital form.

Figure 2:
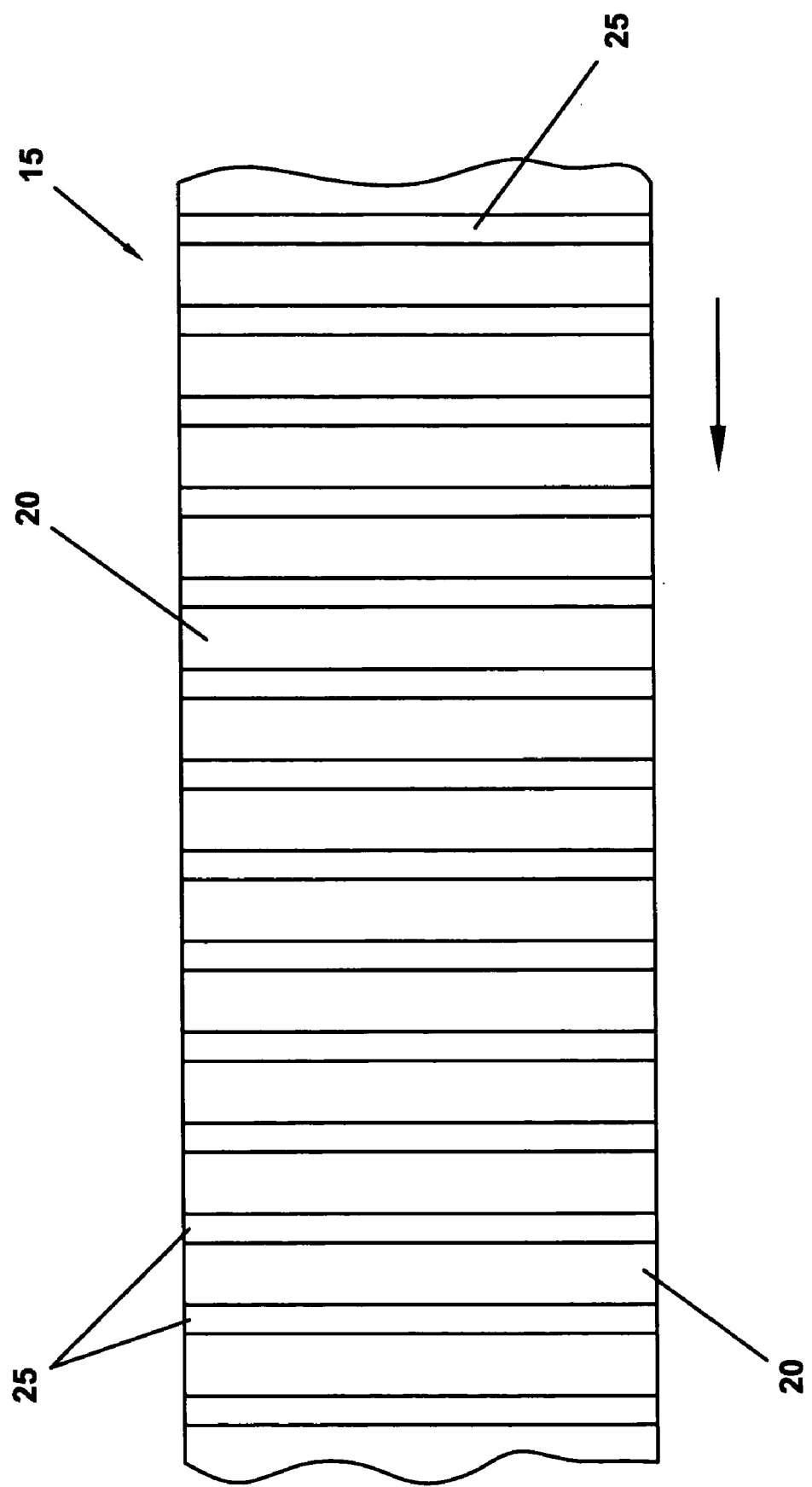
FIG. 2 is a top plan view showing the moving substrate with secondary material deposits of FIG. 1, wherein an X-ray apparatus used by the measurement method of the present invention has been removed for purposes of clarity.

While the method of the present invention can be used to detect and measure a secondary material that is deposited substantially uniformly across the entire surface of a substrate, the method is ideally suited to determining the thickness of a secondary material 25 that is only periodically deposited to the substrate 20. For example, as can be seen in FIGS. 1 and 3a–3b, and more clearly in FIG. 2, the moving sheet of material 15 may have secondary material deposits 25 that occur on the substrate 20 in only intermittent regions. In this particular example, the secondary material deposits 25 are in the form of substantially equidistant rows of narrow width that extend across the width of the substrate 20. It should also be realized that the secondary material deposits 25 may occur on the substrate 20 in configurations other than that shown, and the secondary material may actually be deposited into the substrate. For example, the secondary material deposits 25 may occur at irregular intervals and/or may extend over only a portion of the width of the substrate 20. The secondary material deposits 25 may also occur at angles to the length of the substrate 20 other than the substantially perpendicular orientation shown.

In operation, the moving sheet of material 15 travels from a manufacturing machine, a cutter, a winder/unwinder, or other production equipment, in the direction indicated by the arrow. The X-ray apparatus 10 is located at some point along the direction of travel of the moving sheet of material 15, such that the repetitive, intermittent deposits of secondary material 25 pass through the x-ray beam 35. As the moving sheet of material 15 may be traveling with a relatively high linear velocity, it is desirable that the X-ray apparatus 10 have a fast measurement rate (i.e., be capable of high-speed measurement). A multitude of different measurement rates may be acceptable, depending on the required or desired velocity of the moving sheet of material 15. However, a faster measurement rate allows the velocity of the moving sheet of material 15 to be greater, thereby reducing the time required to process the entire length of the sheet. For example, in one particular embodiment of the method of the present invention, it is desirable that a measurement can be made in as little as approximately one-quarter of one millisecond (0.25 milliseconds). Thus, the method of the present invention is able to measure and analyze a multitude of data points along the length of the sheet of material 15.

As can be seen in FIGS. 3a and 3b, respectively, utilizing an X-ray apparatus having high-speed measurement capability allows for the method of the present invention to detect and measure both the bare substrate 20 (see $t_1$, in FIG. 3a), as well as areas of the moving sheet of material 15 wherein the substrate includes secondary material deposits 25 (see $t_2$ in FIG. 3b). In this manner, X-ray transmission/absorption measurements associated with areas of bare substrate 20 can be compared with X-ray transmission/absorption measurements associated with areas of the substrate having secondary material deposits 25, and the acceptability and/or amount of the secondary material deposits can thus be determined. The measurements may be presented and/or recorded in a number of formats, such as, for example, as a difference in signal voltage, as an absolute thickness of each material, as a difference in thickness $(t_2-t_1)$, as a percentage increase in the thickness of the substrate $[(t_2-t_1)/t_1] \times 100$, as a density, or as a basis weight.

The method of the present invention uses the X-ray absorption or transmission characteristics of the materials of interest in performing its analysis. Thus, depending on the type of output desired, it may be necessary that certain properties of each material to be measured be known. For example, when the method of the present invention is used in the cigarette manufacturing industry to calculate an actual thickness or density of a region of a secondary material deposited to a moving substrate of cigarette paper, it is necessary to know the X-ray transmission or absorption characteristics of both the cigarette paper and the secondary material.

Paper products, such as cigarette paper, are typically classified (or graded) by basis weight: the weight of a particular amount of the paper cut to a specific size. Consequently, specific grades of paper will inherently have different thicknesses associated therewith. These different grades of paper will also have different X-ray absorption and transmission characteristics. Thus, if a known amount of X-ray energy is directed at a paper substrate of known composition, a detected amount of X-ray energy transmitted by the paper can be used to calculate the amount of energy absorbed thereby and, thus, to determine the basis weight (grade) of the paper. The basis weight of the paper can then be correlated to a thickness. Of course, this methodology can also be applied to determine other material characteristics.

In a similar manner, other (non-paper) materials will have particular X-ray absorption and transmission characteristics per a given thickness thereof. For example, secondary materials that may be deposited to a substrate will have particular X-ray absorption and transmission characteristics associated therewith. Such secondary materials will commonly absorb more or less X-ray energy than the substrate. As such, these X-ray absorption and/or transmission properties can be used to calculate the thickness or some other characteristic of the secondary material deposits. More particularly, the thickness of a bare substrate (e.g., paper) adjacent to such a deposit can be determined as described above. The measured decrease in X-ray transmission (increase in absorption) detected when a region of secondary material is exposed to the X-ray beam can then be used along with its absorption/transmission characteristics and the known thickness of the adjacent bare substrate to calculate the thickness or some other characteristic of the secondary material. Alternatively, the difference in detector readings associated with an area of bare substrate and an area of a deposit can simply be used to determine the acceptability of the material deposit.

Exemplary Application

In an exemplary application, the method of the present invention is employed in the manufacture of cigarettes or similar smoking articles. In the cigarette manufacturing process, cigarette paper is typically produced or received in long rolls of some width. Typically, the initial roll of cigarette paper, commonly referred to as a master roll, may be approximately 20,000 meters in length and about 36 inches in width. Of course, other lengths and widths are also possible, and such is not essential to the present invention. Eventually, this roll of paper is reduced in width (such as by cutting) to a dimension that is appropriate for forming the circumference of a rolled cigarette, such as about 25–27 millimeters. This paper roll of reduced width is commonly referred to as a bobbin, which may be approximately 6,500 meters in length.

Recently, there has been considerable interest in producing cigarettes with modified burn characteristics. More specifically, it is now desirable, primarily due to recent legislation, to produce a cigarette that is self-extinguishing. A self-extinguishing cigarette is modified in such a manner that when subjected to static conditions (i.e., not smoked) for a given period of time after lighting, burning will cease. However, the modification undertaken to produce the static self-extinguishing effect should also allow the cigarette to behave normally when smoked. For example, the cigarette should not self-extinguish during normal smoking. To achieve this result, it has been found that small amounts of particular additive(s) can be added to the cigarette paper prior to the addition of tobacco.

Because it is desired that such a cigarette self-extinguish only if left in a static condition (i.e., unsmoked) for a given period of time, it is also desirous that the self-extinguishing additive be deposited onto the cigarette paper in intermittent bands. Consequently, the cigarette paper and self-extinguishing additive (secondary material) deposits may appear substantially as illustrated by the moving sheet of material in FIGS. 1–3b (it should be understood that the dimensions of the substrate 20 and the secondary material deposits 25 shown in the drawing figures have been exaggerated for purposes of clarity). In such a self-extinguishing cigarette manufacturing process, the self-extinguishing additive is repetitively deposited in bands of several millimeters in width that extend substantially perpendicularly across the width of the cigarette paper. A length of bare cigarette paper separates each band of self-extinguishing additive. Typically, this length of bare cigarette paper is several times (e.g., three times) the width of an individual self-extinguishing additive band, although other spacing is also possible.

Because the cigarette paper is generally very thin, it can be appreciated that the thickness of the self-extinguishing additive bands deposited thereon, or therein, is typically minimal. For example, it has been determined that the thickness of self-extinguishing additive required to produce the desired self-extinguishing effect when the cigarette is left in a static condition, without adversely affecting the cigarette's burn characteristics during smoking, is equivalent to approximately only a few percent of the thickness of the cigarette paper. In other words, the self-extinguishing additive deposits should only increase the thickness of the cigarette paper by a few percent. Such bands of self-extinguishing additive may be deposited in various ways. For example, the self-extinguishing additive bands may be deposited to the cigarette paper by a printing process, such as by means of a Gravure Coater, or by a number of other known, or as yet unknown, methods. Consequently, because the secondary material deposits 25 in such a case may be very thin, the method of the present invention must be capable of high-speed detection of even minute differences in thickness. For example, when used in this particular cigarette manufacturing process, the method of the present invention is preferably able to detect and calculate material thickness to a precision of 61% at two standard deviations. Other ranges of precision may be designed for, depending on the particular application.

When used in such an application, it must be realized that the thickness of either the substrate, the additive material, or both, may vary slightly. However, because the method of the present invention measures the moving substrate at a multitude of points along its length, including points immediately adjacent to a band of additive material, such differences in thickness can be accounted for.

In one particular self-extinguishing cigarette manufacturing process, measurement data is collected on the moving supply of cigarette paper at a rate of approximately 10,000 samples per second. The linear velocity of the cigarette paper is such that approximately 100 samples are produced for each 1 linear millimeter of cigarette paper passing through the X-ray apparatus. For this particular cigarette manufacturing process, it has been determined that dividing the moving cigarette paper into approximately 0.8 millimeter sections of length is ideal for analysis. As such, measurement data is collected in groups consisting of 80 consecutive data samples, with each group corresponding approximately to a 0.8 linear millimeter section of moving cigarette paper.

Once a group of 80 consecutive data samples has been collected, the measured values associated therewith are averaged together to create a single data point having a value that is representative of its corresponding 0.8 millimeter section of cigarette paper. This process is performed along substantially the entire length of the moving supply of cigarette paper. Thus, representative data points are calculated and collected in substantially real time, with each data point corresponding to the average value of a particular 0.8 linear millimeter section of the cigarette paper. Consequently, at the aforementioned data collection rate, approximately 8,000,000 total data points will be recorded for a standard bobbin of cigarette paper. The representative data points and their associated values are saved for off-line analysis.

Due to the dimensions of a cigarette to be manufactured from the cigarette paper in this particular process, the data points are analyzed off-line in groups of 32—where each group of 32 data points represents approximately a 25 linear millimeter section of cigarette paper. Each group of 32 data points is analyzed to determine the 8 consecutive data points having the lowest measured values (e.g., lowest voltage readings) associated therewith. These 8 consecutive data points correspond to a linear distance of approximately 6 millimeters, which is the approximate width of an additive material band in this particular process. These 8 consecutive data points of lower measured value are also indicative of an area of increased density and, therefore, the presence of a band of additive material. The remaining data points, which have higher measured values associated therewith, correspond to the bare (lower density) areas of cigarette paper remaining within the approximately 25 millimeter sample length. The values associated with these remaining data points, or some portion thereof, may be used to determine an average cigarette paper density and/or thickness.

Analysis of the groups of 32 data points preferably begins with a group residing near to an end of the cigarette paper supply (bobbin). Because of the repetitive nature of the additive bands, once an initial band is detected, the starting point of the next consecutive band can be found by simply jumping ahead approximately 32 data points into the collection of saved data points.

In addition to locating the bands of additive material, it can be determined whether the amount of additive material present in a detected band is acceptable. The acceptability of an additive material band can be determined by calculating the difference between the measured values of data points corresponding to areas of cigarette paper containing the additive material and the measured values of data points corresponding to adjacent areas of bare cigarette paper. It should be realized that in the simplest form, the difference between measured values could simply be the difference between voltage signals output by the X-ray detector. Such voltage differences could then be used to determine whether the amount of additive material in a given band is adequate by comparing the calculated voltage differences to voltage difference limits determined as a result of laboratory analysis.

If desired, however, the calculated differences between measured values of data points corresponding to areas of bare cigarette paper and the measured values of adjacent data points corresponding to areas of cigarette paper containing the additive material can be used to determine an actual thickness, density, or some other characteristic of one, or both, materials. For example, the actual thickness of an additive material band may be determined by comparing the measured values to data in a lookup table or other database.

Each additive material band deposited on the cigarette paper is analyzed by repeating the above process for subsequent groups of data points corresponding to the remaining length of cigarette paper. Because each band of additive material is associated with a particular set of data points, and the location of each such set of data points along the bobbin of cigarette paper is known, sections of the cigarette paper not suitable for use in manufacturing a self-extinguishing cigarette can be identified. These sections of cigarette paper can then be discarded, or a cigarette manufactured therewith can be marked for rejection.

In the exemplary modified cigarette manufacturing process described above, as well as in other processes to which the method of the present invention may be applied, it is contemplated that the intermittent regions of secondary material 25 may be deposited to substrates 20 of various width. For example, in the above-described cigarette manufacturing process, the self-extinguishing additive bands may be deposited to the cigarette paper either before or after the cigarette paper is cut to proper rolling width. As such, it may be desirable to detect and measure intermittent regions of secondary material 25 of considerably varying length. For example, in the above-described cigarette manufacturing process, it may be desired to measure the self-extinguishing additive bands while the cigarette paper is at its full width (e.g., approximately 36 inches) or, alternatively, after the cigarette paper has been cut to the proper rolling width (e.g., approximately 27 millimeters).

When detecting and measuring intermittent secondary material regions 25 deposited to a substrate 20 of substantially narrow width, it has been found that satisfactory measurements may be obtained by using an X-ray apparatus 10 having only a single emitter 30 and detector 40. For example, the emitter 30 and detector 40 shown in FIGS. 1 and 3a–3b may be positioned substantially along the centerline of the moving sheet of material 15. In such an embodiment, the x-ray beam 35 will typically contact the intermittent regions of secondary material 25 substantially at the midpoint thereof. However, it should be understood that the location of the emitter 30 and detector 40 may also be altered to irradiate substantially any other point along the length of the secondary material regions 25, such as, for example, one end thereof.

When using x-ray emitters such as that described above, a measurement spot of approximately 25 millimeters by 0–4 millimeters may be generated—although other measurement spot sizes and shapes are also possible. When such an emitter 30 is employed, a suitable detector 40 size may be about 25 millimeters by 4 millimeters, in length and width, respectively. Other detector 40 sizes can also be used, depending on the dimensions of the measurement spot produced by the emitter. Consequently, only the area of the moving sheet of material 15 that passes over the detector will be measured by the method of the present invention.

When analyzing a moving sheet of material from a source such as a typical bobbin (i.e., a sheet of approximately 27 millimeters in width), it has been found that examining deposited secondary material regions 25 at only particular (fixed) locations of such a narrow substrate provides for acceptable results. As such, analysis of localized areas of the substrate 20 and each secondary material region 25, typically provides for a satisfactorily accurate measurement of each material across the width of the moving sheet of material 15 at that point.

When additional accuracy is desired, or when, for example, the moving sheet of material 15 and its accompanying regions of secondary material 25 to be measured are of a greater width/length, additional emitters 30 and detectors 40 may be employed. For example, in one exemplary embodiment of the present invention, three emitters 30 and three corresponding detectors 40 may be disposed along the width of the moving sheet of material 15—one emitter/detector pair at approximately its centerline, and one emitter/detector pair at each edge. This arrangement allows for detection and measurement at three points across the width of the moving sheet of material 15. The measurements corresponding to each area of bare substrate 20 and each region of deposited secondary material 25 may then be individually analyzed and/or reported/recorded, or the individual measurement values may be averaged to obtain an approximate average value for the substrate 20 or the respective region of deposited secondary material 25 at a particular length location on the moving sheet of material 15.

Depending somewhat on the linear velocity of the moving sheet of material 15, it is also contemplated that emitter(s) 30 and detector(s) 40 may be located on a moving device (not shown) that traverses back-and-forth along the width direction of the moving sheet of material. Such traversing devices are known, and will not be described in detail herein. The traversing device causes the emitter 30 and detector 40 to be rapidly moved back-and-forth across the width of the moving sheet of material 15, thereby allowing for analysis of the bare substrate 20 as well as areas of the substrate having secondary material deposits 25, at multiple points across the width of the moving sheet of material 15. In this manner, measurements at multiple points across the width of the substrate 20 and along the length of each region of deposited secondary material 25 may be obtained. Consequently, higher accuracy results may be produced without the need to use additional emitters 30 and detectors 40, although multiple emitters and detectors may still be utilized in such an embodiment. The measurement values corresponding to each area of bare substrate 20 and each region of deposited secondary material 25, may then be processed in a manner similar to that described above in regard to the method of the present invention employing multiple-emitters/detectors.

Thus, from the foregoing description of exemplary embodiments of the method of the present invention, it can be seen that the method can be non-exclusively used to accurately detect and measure a secondary material that is intermittently deposited to a moving substrate. The measurement values can be displayed or reported in a variety of ways. Signals from a controller used by the method of the present invention can be utilized to direct secondary material deposition devices or other substrate manufacturing equipment. While certain embodiments of the present invention are described in detail above, the scope of the invention is not to be considered limited by such disclosure, and modifications are possible without departing from the spirit of the invention as evidenced by the following claims:

What is claimed is:

1. A method for detecting and measuring intermittent regions of a secondary material deposited to a moving substrate, said method comprising:
   (a) providing an x-ray source;
   (b) locating said x-ray source on one side of said moving substrate, said x-ray source oriented such that said x-ray source directs a beam of x-ray energy onto said moving substrate;
   (c) providing an x-ray detector;
   (d) locating said x-ray detector on a side of said moving substrate opposite from said side that faces said x-ray source, such that said x-ray detector receives an amount of x-ray energy from said x-ray source that is transmitted through said substrate;
   (e) providing a control system in electronic communication with said x-ray source and said x-ray detector, said control system having a processor and associated software for receiving signals from said x-ray detector as said moving substrate passes thereby;
   (f) receiving at least one signal from said x-ray detector representative of an amount of x-ray energy transmitted by an area of bare substrate adjacent to a region of secondary material;
   (g) receiving at least one signal from said x-ray detector representative of an amount of x-ray energy transmitted by an area of said substrate containing said region of secondary material;
   (h) comparing the value of said signal associated with said area of bare substrate to the value of said signal associated with said area of said substrate containing said secondary material;
   (i) using said comparison of said signals to determine whether said region contains an acceptable amount of said secondary material; and
   (j) repeating steps (f)–(i) for subsequent regions of secondary material that pass by said x-ray detector.

2. The method of claim 1, wherein multiple signals from said x-ray detector are received and grouped together, said group of signals corresponding to a particular section of said moving substrate.

3. The method of claim 2, further comprising averaging together values associated with each signal within said group to produce a single data point having a value representative of an amount of x-ray energy transmitted by said section of said moving substrate.

4. The method of claim 3, wherein the length of said moving substrate is divided into a plurality of consecutive linear sections, with a representative data point produced for each section and saved for off-line analysis.

5. The method of claim 4, further comprising grouping together data points representative of some predetermined number of consecutive linear sections of said moving substrate, such that each group of data points corresponds to a particular length of said moving substrate.

6. The method of claim 5, further comprising analyzing the value of each data point in a group of data points to identify a consecutive number of data points having a value lower than the remainder of said data points, said consecutive number of data points of lower value corresponding to an area of said moving substrate containing said secondary material.

7. The method of claim 6, wherein said regions of secondary material are repetitively deposited at substantially equal intervals on said substrate.

8. The method of claim 7, further comprising locating a successive region of said secondary material by moving ahead in said collection of data points from approximately an initial one of said consecutive number of data points having a value lower than the remainder of said data points in its group, a number of data points whose collective representative substrate length corresponds approximately to said interval between said regions of secondary material.

9. The method of claim 1, wherein acceptability of a region of secondary material is determined by calculating a difference in voltage between said signals received from said detector for an area of said substrate containing said secondary material and an adjacent area of bare substrate, respectively, and comparing said voltage difference with a predetermined range of acceptable voltage differences.

10. The method of claim 1, wherein a thickness of said bare substrate and/or a region of secondary material can be determined by comparing the amount of x-ray energy transmitted or absorbed thereby with predetermined x-ray transmission and/or absorption data for specific thicknesses of the respective material.

11. The method of claim 1, wherein said x-ray source and said x-ray detector are located to impinge said moving supply of material at approximately the centerline thereof.

12. The method of claim 1, wherein said x-ray source and said x-ray detector are located to impinge said moving supply of material at, or near, one edge thereof.

13. The method of claim 1, wherein said x-ray source and said x-ray detector are mounted on an apparatus that moves said x-ray source and said x-ray detector in unison back-and-forth across said moving supply of material in a direction substantially transverse to the length thereof.

14. The method of claim 1, further comprising multiple x-ray sources and corresponding x-ray detectors arranged transversely across said moving sheet of material.

15. The method of claim 1, wherein a signal is received from said x-ray detector approximately every 0.25 milliseconds.

16. The method of claim 1, further comprising providing communication with a means for depositing said secondary material onto said substrate, said means for depositing said secondary material onto said substrate adjustable in response to signals from said control system.

17. The method of claim 1, wherein unacceptable regions of secondary material can be identified and located on said substrate.

18. The method of claim 1, wherein the thickness of said regions of secondary material is between about 4%–6% of the thickness of said substrate.

19. The method of claim 1, wherein said intermittent regions of secondary material occur at irregular intervals.

20. A method for detecting and measuring regions of a burn-characteristic-modifying material deposited at intermittent intervals to a moving web of smoking article paper, comprising:

providing an x-ray source;

locating said x-ray source on one side of said moving web of smoking article paper, said x-ray source oriented such that said x-ray source directs a beam of x-ray energy onto said moving web of smoking article paper;

providing an x-ray detector;

locating said x-ray detector on a side of said moving web of smoking article paper opposite from said side that faces said x-ray source, such that said x-ray detector receives an amount of x-ray energy from said x-ray source that is transmitted through said moving web of smoking article paper;

(e) providing a control system in electronic communication with said x-ray source and said x-ray detector, said control system having a processor and associated software for receiving signals from said x-ray detector as said moving web of smoking article paper passes thereby;

(f) receiving at least one signal from said x-ray detector representative of an amount of x-ray energy transmitted by an area of bare smoking article paper adjacent to a region of said burn-characteristic-modifying material;

(g) receiving at least one signal from said x-ray detector representative of an amount of x-ray energy transmitted by an area of said smoking article paper containing said region of burn-characteristic-modifying material;

(h) comparing the value of said signal associated with said area of bare smoking article paper to the value of said signal associated with said area of smoking article paper containing said region of burn-characteristic-modifying material;

(i) using said comparison of signals to determine whether said region contains an acceptable amount of said burn-characteristic-modifying material; and (j) repeating steps (f)–(i) for subsequent regions of burn-characteristic-modifying material that pass by said x-ray detector.

21. The method of claim 20, wherein multiple signals from said x-ray detector are received and grouped together, said group of signals corresponding to a particular section of said web of smoking article paper.

22. The method of claim 21, further comprising averaging together values associated with each signal within said group to produce a single data point having a value representative of an amount of x-ray energy transmitted by said section of smoking article paper.

23. The method of claim 22, wherein the length of said web of smoking article paper is divided into a plurality of consecutive linear sections, with a representative data point produced for each section and saved for off-line analysis.

24. The method of claim 23, further comprising grouping together data points representative of some predetermined number of consecutive linear sections of said web of smoking article paper, such that each group of data points corresponds to a particular length of smoking article paper.

25. The method of claim 24, further comprising analyzing the value of each data point in a group of data points to identify a consecutive number of data points having a value lower than the remainder of said data points, said consecutive number of data points of lower value corresponding to an area of said web of smoking article paper containing said burn-characteristic-modifying material.

26. The method of claim 25, wherein said regions of burn-characteristic-modifying material are repetitively deposited at substantially equal intervals on said web of smoking article paper.

27. The method of claim 26, further comprising locating a successive region of said burn-characteristic-modifying material by moving ahead in said collection of data points from approximately an initial one of said consecutive number of data points having a value lower than the remainder of said data points in its group, a number of data points whose collective representative length corresponds approximately to said interval between said regions of burn-characteristic-modifying material.

28. The method of claim 20, wherein acceptability of a region of burn-characteristic-modifying material is determined by calculating a difference in voltage between said signals received from said x-ray detector for an area of said smoking article paper containing said burn-characteristic-modifying material and an adjacent area of bare smoking article paper, respectively, and comparing said voltage difference with a predetermined range of acceptable voltage differences.

29. The method of claim 20, wherein a thickness of said bare smoking article paper and/or a region of burn-characteristic-modifying material can be determined by comparing the amount of x-ray energy transmitted or absorbed thereby with predetermined x-ray transmission and/or absorption data for specific thicknesses of the respective material.

30. The method of claim 20, wherein said x-ray source and said x-ray detector are located to impinge said moving web of smoking article paper at approximately the centerline thereof.

31. The method of claim 20, wherein said x-ray source and said x-ray detector are located to impinge said moving web of smoking article paper at, or near, one edge thereof.

32. The method of claim 20, wherein said x-ray source and said x-ray detector are mounted on an apparatus that moves said x-ray source and said x-ray detector in unison back-and-forth across said moving web of smoking article paper in a direction substantially transverse to the length thereof.

33. The method of claim 20, further comprising multiple x-ray sources and corresponding x-ray detectors arranged transversely across said moving web of smoking article paper.

34. The method of claim 20, wherein a signal is received from said detector approximately every 0.25 milliseconds.

35. The method of claim 20, further comprising providing communication with a means for depositing said burn-characteristic-modifying material onto said moving web of smoking article paper, said means for depositing said burn-characteristic-modifying material onto said web of smoking article paper adjustable in response to signals from said control system.

36. The method of claim 20, wherein unacceptable regions of burn-characteristic-modifying material can be identified and located on said web of smoking article paper.

37. The method of claim 20, wherein the thickness of said regions of burn-characteristic-modifying material is between about 4%–6% of the thickness of said smoking article paper.

38. The method of claim 20, wherein said intermittent regions of burn-characteristic-modifying material occur at irregular intervals.

39. A method for detecting and measuring deposits of a burn-characteristic-modifying material occurring at repetitive and substantially equally spaced intervals to a moving web of smoking article paper, comprising:

(a) providing an x-ray source;

(b) locating said x-ray source on one side of said moving web of smoking article paper, said x-ray source oriented such that said x-ray source directs a beam of x-ray energy onto said moving web of smoking article paper;

(c) providing an x-ray detector;

(d) locating said x-ray detector on a side of said moving web of smoking article paper opposite from said side that faces said x-ray source, such that said x-ray detector receives an amount of x-ray energy from said x-ray source that is transmitted both through a bare portion of said moving web of smoking article paper, and through a portion of said moving web of smoking article paper containing an amount of said burn-characteristic-modifying material;

(e) providing a control system in electronic communication with said x-ray source and said x-ray detector, said control system having a processor and associated software for receiving signals from said x-ray detector as said moving web of smoking article paper passes thereby;

(f) receiving signals from said detector representative of an amount of x-ray energy transmitted by an area of bare smoking article paper adjacent to a deposit of burn-characteristic-modifying material;

(g) receiving signals from said detector representative of an amount of x-ray energy transmitted by an area of said smoking article paper containing said deposit of burn-characteristic-modifying material;

(h) dividing said web of smoking article paper lengthwise into a plurality of consecutive linear sections;

(i) grouping together multiple signals from said detector, a group of signals corresponding to each of said consecutive linear sections of said moving web of smoking article paper;

(j) averaging together values associated with said signals within each group to produce a single data point having a value representative of an amount of x-ray energy transmitted by a corresponding section of said moving web of smoking article paper;

(k) saving said data points for off-line analysis;

(l) subsequently, collecting said saved data points in groups corresponding to some predetermined number of said consecutive linear sections of said moving web of smoking article paper, such that each group of data points equates to a particular length along said web of smoking article paper;

(m) analyzing a value associated with each data point in a group of data points to identify a consecutive number of data points having a value lower than the remainder of said data points in said group, said consecutive number of data points of lower value corresponding to an area of said smoking article paper containing said burn-characteristic-modifying material;

(n) comparing the value of said data points associated with said area of bare smoking article paper to the value of said data points associated with said area of said smoking article paper containing said burn-characteristic-modifying material;

(o) using said comparison of said data point values to determine whether a deposit contains an acceptable amount of said burn-characteristic-modifying material; and (p) repeating steps (m)–(o) for remaining groups of data points along the length of said web of smoking article paper.

40. The method of claim 39, further comprising locating a successive deposit of said burn-characteristic-modifying material by moving ahead in said collection of data points from approximately an initial one of said consecutive number of data points having a value lower than the remainder of said data points in its group, a number of data points whose collective representative smoking article paper length corresponds approximately to said interval between said deposits of burn-characteristic-modifying material.

* * * * *